US00PP13818P29

(12) United States Plant Patent
Holtkamp, Sr.

(10) Patent No.: US PP13,818 P2
(45) Date of Patent: May 13, 2003

(54) AFRICAN VIOLET PLANT NAMED 'EVERGRACE'

(75) Inventor: Reinhold Holtkamp, Sr., Nashville, TN (US)

(73) Assignee: International Plant Breeding AG, Liebefeld (CH)

( * ) Notice: Subject to any disclaimer, the term of this patent is extended or adjusted under 35 U.S.C. 154(b) by 0 days.

(21) Appl. No.: 10/046,747

(22) Filed: Jan. 17, 2002

(51) Int. Cl.[7] ..... A01H 5/00
(52) U.S. Cl. ..... Plt./270

(58) Field of Search ..... Plt./270

*Primary Examiner*—Kent Bell
(74) *Attorney, Agent, or Firm*—Foley & Lardner

(57) ABSTRACT

A new and distinct cultivar of African Violet named 'EverGrace' particularly characterized by its multiflorescence trait, single, violet-shaped white flowers with variable amounts of light blue in the center and around the edges, frilled light green edges; strong, upright flower stems that curve slightly toward the center to form a compact flower bouquet above the leaves; medium green, wavy, heart-shaped leaves; vigorous and extra large growth habit; flowering 12–13 weeks after potting, and long-lasting and non-dropping flowers.

1 Drawing Sheet

LATIN NAME OF THE GENUS AND SPECIES OF THE PLANT CLAIMED

*Saintpaulia ionantha.*

VARIETY DENOMINATION

'EverGrace'.

BACKGROUND OF THE INVENTION

The present invention comprises a new and distinct cultivar of African Violet plant, botanically known as *Saintpaulia ionantha*, and hereinafter referred to by the cultivar name 'EverGrace'.

The new cultivar was referred to during the breeding and selection process by the designation 'R 7/1 B' and is a product of a planned breeding program. The new cultivar is a mutation of *Saintpaulia ionantha* 'EverPraise' (U.S. Plant patent application Ser. No. 10/046,985) discovered by the inventor, Reinhold Holtkamp, Sr., in the controlled breeding program Nashville, Tenn. The female, or seed grandparent was a cultivar designated 'SB 4-2 Muflo' (U.S. Plant Patent application Ser. No. 10/046,968). The male, or pollen grandparent was a cultivar designated 'P 6/6' (unpatented). 'SB 4-2 Muflo' was produced from plants derived from African Violet seeds incubated in a weightless environment in space on the Long Duration Exposure Facility.

In comparison to 'EverGrace', 'SB 4-2 Muflo' is a multiflorescent cultivar having single, violet-shaped medium blue flowers. The leaves of 'SB 4-2 Muflo' are medium green which in contrast to the leaves of 'EverGrace' are not wavy, nor crenate. Unlike 'EverGrace', the petals of 'SB 4-2 Muflo' do not have the light green edge, and the flowers are not bi-colored. In comparison to 'EverGrace', 'P 6/6' is a cultivar having single, violet-shaped, non-multiflorescent burgundy flowers. Similar to 'EverGrace'the petals of 'P 6/6' have a light green edge.

'EverGrace' was discovered and selected by the inventor as a flowering plant within a planting of 'EverPraise' in a controlled environment in Nashville, Tenn. Asexual reproduction of the new cultivar by leaf cuttings, as performed by the inventor in Nashville, Tenn., has demonstrated that the combination of characteristics as herein disclosed for the new cultivar are firmly fixed and retained through successive generations of asexual reproduction. The new cultivar reproduces true-to-type.

'EverGrace' has not been observed under all possible environmental conditions. The phenotype may vary significantly with variations in environment such as temperature, light intensity and day length without a change in genotype. The following observations, measurements and values describe the new cultivar as grown in Nashville, Tenn. and Haffen, Germany under greenhouse conditions which closely approximate those generally used in commercial practice.

BRIEF SUMMARY OF THE INVENTION

The following characteristics have been repeatedly observed and are determined to be basic characteristics of 'EverGrace', which in combination distinguish this African Violet as a new and distinct cultivar:

1) Multiflorescence;

2) A single crown as large as 35–45 cm in diameter;

3) Strong, upright flower stems curving slightly toward the center;

4) Single violet-shaped white flowers with variable amounts of light blue in the center fading towards the edges and around some flower edges; frilled light green edges, especially on the two smaller petals;

5) Each plant carries approximately 12–16, sometimes more, upright flower stems each of which carry 10–14, sometimes more flowers;

6) Long-lasting, non-dropping flowers;

7) Vigorous and compact grower;

8) Plant saleable 12–13 weeks after potting;

9) Seed capsules visible above the petals;

10) Medium-green, wavy, heart-shaped leaves; and

11) After maturity the flowers dry off, and remain on the peduncle without becoming infected by Botrytis.

The new cultivar is most similar to 'EverPraise' (U. S. Plant patent application Ser. No. 10/046,985). Both 'EverGrace' and 'EverPraise' display the multiflorescence trait, have the same extra large growth habit and same type leaves and flower shape with the greenish edge. However, 'EverPraise' has medium blue flowers whereas 'EverGrace' has bi-colored flowers, white with variable amounts of light blue in the center, fading out to the edges and around some edges. In addition, 'EverGrace' has a wider green edge than 'EverPraise'.

BRIEF DESCRIPTION OF THE DRAWING

The accompanying color photographic drawing shows a typical plant of the new cultivar 'EverGrace'. The colors appearing in the photographic drawing are as true as possible with color illustrations of this type. The photographic drawing is a top view of 'EverGrace' depicting the leaves and flowers.

DETAILED BOTANICAL DESCRIPTION

In the following description, color references are made to The Royal Horticultural Society Colour Chart (R.H.S.), except where general colors of ordinary significance are referred to. Color values were taken under natural sunlight conditions at approximately 12 p.m. in Nashville, Tenn. Measurements were taken 16–18 weeks from potting, as grown in a 6" pot.

Parentage: Mutation of *Saintpaulia ionatha, Ramat* 'EverPraise'.

Propagation: Leaf cuttings.

Plant: 12 cm to 14 cm tall when grown in pots, and 35–45 cm in diameter when fully grown.

*Leaves.*—General form: Heart-shaped. Leaf margin: Crenate. Apex: Emarginate. Size: 90–105 mm wide and 95–110 mm long. Texture: Leatherlike. Aspect: Wavy, serrated, hairy, shiny. Veins: Upperside: visible, between RHS 147 A and RHS 147 B; underside: well pronounced light green, RHS 147 D, shiny. Color (upperside): Yellow-Green RHS 147 A. Color (underside): Greyed-Green RHS 194 C to RHS 194 D. Petiole: Strong, light green, between RHS 147 C and RHS 146 C, hairy.

*Flowers.*—Buds: Bell-shaped, greenish white, between RHS 147 C and RHS 145 D, 8–10 mm in length, and 7–8 mm in width just before opening. Sepals: Five (5), one for each flower petal, spear shaped, 4–6 mm in length, 1.5 to 2 mm in width at the base and 0.5 to 1 mm in width at the tips, margins are entire; both upper and underside color light green, between RHS 147 B and RHS 146 B. Calyx: Shape: Funnel-shaped. Peduncle: Character: Strong upright, hairy; 20–25 mm in length, 1 mm in diameter; color light green, RHS 147 C, with an occasional touch of brown, RHS 177 A.

*Individual flowers.*—Size: 35–40 mm in width (as measured when pressed flat), 30–35 mm in length (as measured from the top of the small petals to the bottom of the large middle petal). Shape: Single violet-shaped with finely frilled edges. Petals: Violet-shaped, five (5 total, 3 large, 2 small); small petals are 12–14 mm in length and 10–13 mm in width; large petals are 18–22 mm in length and 15–18 mm in width; margins are wavy and finely frilled; rounded apex shape. Color (upperside): White with variable amounts of violet-blue RHS 89 D on some edges and in the center fading out to a lighter color, closest to between RHS 91 B and RHS 91 C towards the petals. Green edges are yellow-green RHS 145 B to RHS 145 C. Occasionally, the green edge is lacking. Under cooler temperatures and more intensive lighting, the light blue tends to intensify. Color (underside): White with touches of violet RHS 88 D and lighter on some edges, fading to to between RHS 91 C and RHS 91 D. Green edges are yellow-green RHS 145 B to RHS 145 D. Borne: Each flower stem carries 10–14 and more flowers on strong, upright peduncles that are free standing above the leaves, thereby forming a compact bouquet. Flowering habit: Flowers 12–13 weeks after potting. Lastingness of the individual bloom: 4–6 weeks under good growing conditions.

*Reproductive organs.*—Stamens: Two (2), 2 anthers composed of 4 anther cells, seed capsules push slightly through. Pistil: One (1). Filaments: Yellowish white, 3–4 mm long. Pollen Color: Yellow RHS 7 A; moderate pollen production. Styles: 7–8 mm long, light blue, base of ovary light green and hairy.

*Roots.*—Normally developed, white when young, turning slightly brownish when older.

Disease resistance: 'EverGrace' has shown very good resistance to all major violet diseases.

General observations: 'EverGrace' is a very attractive cultivar due to its abundance of mostly white flowers with variable amounts of light blue in the center, radiating into the petals and around some petal edges and a distinctive light green frilled edge, especially on the two smaller petals. Furthermore, it is an outstanding cultivar due to its multiflorescence trait in which a plant has 2 to 3 flower stems emerging out to each leaf internode, thereby giving the cultivar continuously new buds before the old flowers have wilted. A nice flower bouquet is free-standing above the leaves which develops 12–13 weeks after planting a rooted plantlet. Under ideal growing conditions, 'EverGrace' is never without blooms. Each of the 12–16 , or more, strong flower stems carries 10–14, or more, single violet-shaped flowers with frilled edges. 'EverGrace' is an extra large cultivar, designed to be grown in a 15 cm pot. The plant also may be successfully grown in a 10 cm pot within a 8–10 week time period from potting to finish. The profuse flower bouquet is surrounded by large, medium-green, heart-shaped, wavy leaves. The flowers are long-lasting and non-dropping and the seed capsules push slightly through.

I claim:

1. A new and distinct African Violet plant named 'EverGrace', as described and illustrated herein.

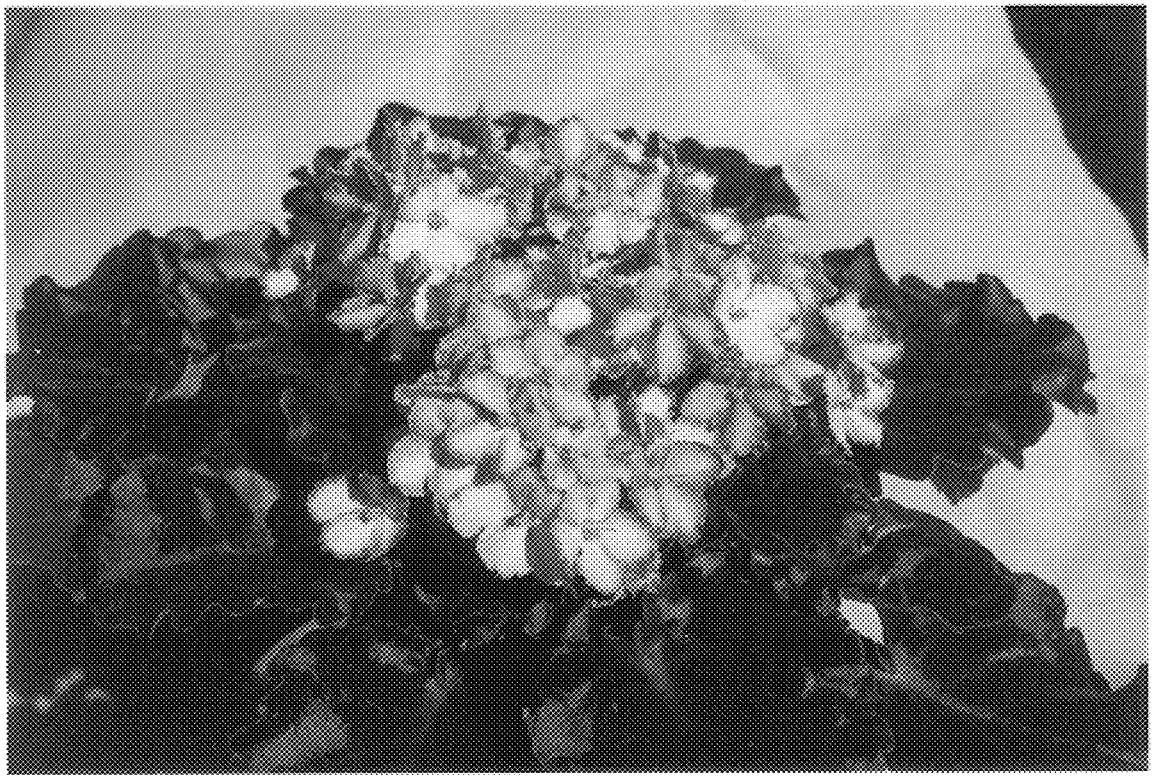

* * * * *